(12) United States Patent
Eyal et al.

(10) Patent No.: US 11,395,842 B2
(45) Date of Patent: Jul. 26, 2022

(54) PURIFIED CANNABIS EXTRACTS AND METHODS FOR PRODUCTION THEREOF

(71) Applicant: BUZZELET DEVELOPMENT AND TECHNOLOGIES LTD, Or-Akiva (IL)

(72) Inventors: Aharon M. Eyal, Jerusalem (IL); Dana Berneman Zeitouni, Kfar Yona (IL)

(73) Assignee: BUZZELET DEVELOPMENT AND TECHNOLOGIES LTD, Or Akiva (IL)

( * ) Notice: Subject to any disclaimer, the term of this patent is extended or adjusted under 35 U.S.C. 154(b) by 0 days.

(21) Appl. No.: 16/958,715

(22) PCT Filed: Dec. 21, 2018

(86) PCT No.: PCT/IB2018/060541
§ 371 (c)(1),
(2) Date: Jun. 28, 2020

(87) PCT Pub. No.: WO2019/130201
PCT Pub. Date: Jul. 4, 2019

(65) Prior Publication Data
US 2021/0008138 A1     Jan. 14, 2021

Related U.S. Application Data

(60) Provisional application No. 62/612,162, filed on Dec. 29, 2017.

(51) Int. Cl.
*A61K 36/00* (2006.01)
*A61K 36/185* (2006.01)
*A61K 31/05* (2006.01)

(52) U.S. Cl.
CPC ............ *A61K 36/185* (2013.01); *A61K 31/05* (2013.01)

(58) Field of Classification Search
None
See application file for complete search history.

(56) References Cited

U.S. PATENT DOCUMENTS

2010/0119606 A1* 5/2010 Whittle .................. A61K 31/05
424/484

OTHER PUBLICATIONS

International Preliminary Report on Patentability for PCT/IB2018/060541 dated Mar. 26, 2019.
International Search Report for PCT/IB2018/060541 dated Apr. 15, 2019.

* cited by examiner

*Primary Examiner* — Michael V Meller
(74) *Attorney, Agent, or Firm* — Alphapatent Associates, Ltd; Daniel J. Swirsky

(57) ABSTRACT

A method for producing a purified cannabis extract includes providing a first extract with an organic hydrophilic solvent, at least one cannabinoid, and water at concentration $W_1$ by weight, and at least one impurity at impurity to cannabinoid weight/weight ratio R1; adding water to the first extract to reach water concentration $W_2$ by weight, whereby a solid matter and a second extract are formed; separating the solid matter from the second extract, whereby separated solid matter and separated second extract are formed. The separated second extract includes the organic hydrophilic solvent, the at least one cannabinoid, and water to cannabinoid weight/weight ratio $R_2$.

4 Claims, No Drawings

PURIFIED CANNABIS EXTRACTS AND METHODS FOR PRODUCTION THEREOF

BACKGROUND OF THE INVENTION

Among medical cannabis patients, the fraction that consumes their cannabis by smoking keeps decreasing. As an alternative, more patients use today extracts as such, e.g. sublingually or in a vaporizer. Cannabis extracts are also used as a staring material for the production of other medical cannabis formulations, such as tablets, suppositories, topicals, patches and sprays.

Cannabis extracts are produced by contacting cannabis plant material with a suitable extractant to form an extractant-containing extract followed by removing the extractant from that extractant-containing extract to form the cannabis extract. Selection of the extractant and of the extraction protocol are typically driven by economics considerations, i.e. an optimal combination of high extraction yield and low capital and operating costs.

Given that cannabis therapeutic active components are lipophilic in nature, extractants are composed of organic solvents of various polarities, ranging between ethanol and butane, including alkanols, ethers and super-critical $CO_2$ (SCCO2). Extractant properties affect extraction selectivity, including co-extraction of impurities resulting from the plant material. Those impurities may include toxic contaminants, such as pesticides or herbicides (if used in cultivation) and/or components that affect the flavor, the color and/or the clarity of the extract and/or components that affect formulation of the extract.

Currently, there is a tradeoff, producing extracts of high purity requires highly expensive extraction methods, e.g. SCCO2, where capital costs are high. There is therefore a strong need for the production of high purity extracts at lower costs, particularly in those cases where therapy requires administering high doses of extracts or products thereof.

SUMMARY OF THE INVENTION

Provided is a method for producing a purified cannabis extract comprising (i) providing a first extract comprising an organic hydrophilic solvent, at least one cannabinoid, water at concentration $W1$ by weight, optionally at least one terpene, optionally wax, and at least one impurity at impurity to cannabinoid weight/weight ratio $R1$; (ii) adding water to said first extract to reach water concentration $W2$ by weight, whereby a solid matter and a second extract are formed; (iii) separating said solid matter from said second extract, whereby separated solid matter and separated second extract are formed, wherein separated second extract comprises said organic hydrophilic solvent, said at least one cannabinoid, water, optionally at least one terpene and optionally said at least one impurity at impurity to cannabinoid weight/weight ratio $R2$; and optionally (iv) separating organic hydrophilic solvent from said second extract; wherein (a) the solubility of said organic hydrophilic solvent in water at 200° C. is at least 20 gram solvent per 100 gram water; (b) $W2/W1$ is greater than 1.1; and (c) $R2/R1$ is less than 0.9.

According to an embodiment, said impurity comprises a cannabis plant material component other than cannabinoids, terpenes and waxes.

According to an embodiment, said solvent comprises ethanol and $W1$ is less than 20% by weight. According to an embodiment, said solvent comprises ethanol and $W2$ is less than 40% by weight.

According to an embodiment, said providing a first extract comprises contacting cannabis plant material with an extractant, wherein said extractant comprises said organic hydrophilic solvent.

According to an embodiment, said cannabinoid amount in said first extract is $C1$, cannabinoid amount in said second extract is $C2$, and $C2/C1$ is greater than 0.5.

According to an embodiment, said method further comprises maintaining said first extract at a temperature of less than zero degrees Celsius for a duration of at least 1 hour before said adding water, concurrently with said adding water or after said adding water.

According to an embodiment, said organic hydrophilic solvent comprises ethanol, $W1$ is in a range between 5% and 20% by weight and $W2$ is in the range between 20% and 40% by weight.

According to an embodiment, further provided is a purified cannabis extract produced according to said method, which purified extract is characterized by having a lighter color compared with that of an extract produced similarly, except for adding one half the amount of water. According to an embodiment, further provided is a purified cannabis extract produced according to the method of Claim 1, which purified extract is characterized by having a less astringent flavor compared with that of an extract produced similarly, except for adding one half the amount of water.

According to an embodiment, said separated solid matter comprises at least one cannabinoid and said method further comprises combining said separated solid matter with a cannabinoid-comprising composition.

According to an embodiment, said separated solid matter comprises at least one cannabinoid and said method further comprises contacting said separated solid matter with an organic solvent, whereby a third extract is formed and combing said third extract with a cannabinoid-comprising composition.

According to an embodiment, further provided is a method for producing a purified cannabis extract comprising (i) providing a cannabis plant material comprising at least one cannabinoid and at least one impurity at impurity to cannabinoid weight/weight ratio $R3$; (ii) contacting said cannabis plant material for a duration of at least 0.1 minute, with an extractant comprising an organic hydrophilic solvent and $W3$ water, wherein the temperature of said extractant is $T1$, whereby a fourth extract and residual plant material are formed, which fourth extract comprises said organic hydrophilic solvent, at least one cannabinoid, water, optionally at least one terpene, optionally wax, and at least one impurity at impurity to cannabinoid weight/weight ratio $R4$; and (iii) separating said fourth extract from said residual plant material, wherein (a) said organic hydrophilic solvent is fully miscible with water at $T1$ and $W3$ is greater than 10% by weight, or the solubility of said organic hydrophilic solvent in water at $T1$ is at least 20 gram solvent per 100 gram water and $W3$ is at least one tenth of saturation water concentration at $T1$; (b) $T1$ is sub-zero Celsius; and (c) $R4/R3$ is less than 0.9.

According to an embodiment, said method further comprises (i) adding water to said fourth extract to reach water concentration $W4$ by weight, whereby a solid matter and a fifth extract are formed; which fifth extract comprises said organic hydrophilic solvent, said at least one cannabinoid, water, optionally at least one terpene and optionally said at least one impurity at impurity to cannabinoid weight/weight ratio R5; (ii) separating said solid matter from said fifth extract, whereby separated solid matter and separated fifth extract are formed; and optionally (iii) separating organic hydrophilic solvent from said fifth extract; wherein (a) W4/W3 is greater than 1.1; and (b) R5/R4 is less than 0.9.

According to an embodiment, said impurity comprises a cannabis plant material component other than cannabinoids, terpenes and waxes.

According to an embodiment, cannabinoid amount in said fourth extract is C3, cannabinoid amount in said fifth extract is C4, and wherein C4/C3 is greater than 0.5.

According to an embodiment, said method further comprises maintaining said fourth extract at a temperature of less than zero degrees Celsius for a duration of at least 1 hour before said adding water, concurrently with said adding water or after said adding water.

According to an embodiment, said hydrophilic organic solvent comprises ethanol and W3 is in the range between 5% and 40% by weight.

According to an embodiment, further provided is a purified cannabis extract produced according to said method, which extract is characterized by having a lighter color compared with that of an extract produced similarly, except for using an extractant with one half W3 water, except for contacting with an extractant at a temperature of above zero Celsius or both. According to another embodiment, further provided is a purified cannabis extract produced according to said method, which extract is characterized by having a less astringent flavor compared with that of an extract produced similarly, except for using an extractant with one half W3 water, except for contacting with an extractant at a temperature of above zero Celsius or both.

DETAILED DESCRIPTION OF THE INVENTION

Unless indicated otherwise, percent is weight percent and ratio is weight/weight ratio. Unless indicated otherwise, weight ratio means the ratio between weight content, e.g. in an aqueous solution containing 20% solute and 80% water, the solute to water weight ratio is 20:80 or 1:4.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Provided are methods for producing purified extracts and purified extracts generated therefrom. According to some embodiments, said extracts result from extracting cannabis plant material. All extracts and plant materials comprise at least one cannabinoid. As known in the art, cannabinoids have an acid form and a non-acid form (which is also referred to as the decarboxylated form, since it can be generated by decarboxylating the acid form). The acid form is indicated herein by the letter (a) at the end of the cannabinoid acronym, e.g. tetrahydrocannabiniolic acid is indicated as THCa, while the decarboxylated form is THC According to an embodiment, at least one of the cannabinoids is in acid form. According to an embodiment, at least one of the cannabinoids is at least partially in decarboxylated form. According to an embodiment, at least 50% of the cannabinoid is in decarboxylated form, at least 60%, at least 70%, at least 80% or at least 90%. Unless indicated otherwise, naming a cannabinoid refers to both its acid and decarboxylated forms.

According to an embodiment, said cannabinoid is selected from the group consisting of tetrahydrocannabiniol (THCa and/or THC), cannabidiol (CBDa and/or CBD), cannabigerol (CBGa and/or CBG), cannabichromene (CBCa and/or CBC) tetrahydrocannabivarin (THCVa and/or THCV), Cannabidivarin (CBDVa and/or CBDV), cannabinol (CBNa and/or CBN, respectively) and combinations thereof.

According to an embodiment, said extracts and/or plant materials comprise at least one terpene. The term "terpene", as used herein, refers to both terpenes and terpenoids. According to an embodiment, said terpene is selected from the group consisting of pinene, limonene, linalool, caryophyllene, myrcene, humulene, borneol, eucalyptol, terpineol, nerolidol, phytol, geraniol, bisabolol, camphene, betaamyrin, thujone, citronellol, pulegone, cycloartenol, isomers thereof and combinations thereof. According to an embodiment, said terpene is a-cyclic. According to an embodiment, said terpene is cyclic. According to an embodiment, said terpene is monoterpene, sesquiterpene, diterpene or a combination thereof. According to an embodiment, said terpene comprises at least one hydroxy-terpene. As used herein "hydroxy-terpene" refers to a terpene carrying a hydroxyl function.

Provided is a method for producing a purified cannabis extract comprising (i) providing a first extract comprising an organic hydrophilic solvent, at least one cannabinoid, water at concentration W1 by weight, optionally at least one terpene, optionally wax, and at least one impurity at impurity to cannabinoid weight/weight ratio R1; (ii) adding water to said first extract to reach water concentration W2 by weight, whereby a solid matter and a second extract are formed; (iii) separating said solid matter from said second extract, whereby separated solid matter and separated second extract are formed, wherein said separated second extract comprises said organic hydrophilic solvent, said at least one cannabinoid, water, optionally at least one terpene and optionally said at least one impurity at impurity to cannabinoid weight/weight ratio R2; and optionally (iv) separating organic hydrophilic solvent from said second extract; wherein (a) the solubility of said organic hydrophilic solvent in water at 200° C. is at least 20 gram solvent per 100 gram water; (b) W2/W1 is greater than 1.1; and (c) R2/R1 is less than 0.9.

According to an embodiment, said providing a first extract comprises contacting cannabis plant material with an extractant, wherein said extractant comprises said organic hydrophilic solvent, for at least 0.5 minute, then removing the residual plant material, whereby a preliminary extract is formed. According to an embodiment, said preliminary extract is used as said first extract. Alternatively, said providing further comprises treating said preliminary extract, whereby said first extract is formed. According to an embodiment, said treating comprises at least one of filtration and partial removal of said organic hydrophilic solvent, e.g. removing 25%, 50% or 75% of said solvent. According to an embodiment, the moisture content of said contacted cannabis plant material is less than 25%.

According to an alternative embodiment, said providing a first extract comprises contacting cannabis plant material with condensed gas under super-atmospheric pressure for at least 0.5 minute, removing the residual plant material to form condensed-gas extract, removing at least a fraction of said condensed gas to form a desolventized extract and mixing said desolventized extract with said organic hydrophilic solvent.

According to an embodiment, said extractant comprises said organic hydrophilic solvent. According to an embodiment, said organic hydrophilic solvent forms at least 60% of said extractant, at least 70% or at least 80%. According to an embodiment, said extractant further comprises water. According to an embodiment, said organic hydrophilic solvent forms an azeotrope with water and water concentration in said extractant is greater than that in the azeotrope at same temperature and pressure.

According to an embodiment, the boiling point of said organic hydrophilic solvent is less than 100 degrees Celsius. According to an embodiment, the solubility of said organic hydrophilic solvent in water at 20° C. is at least 20 gram solvent per 100 gram of water, at least 30, at least 40, at least 50, at least 60, at least 70 or at least 80 gram solvent per 100 gram of water. According to an embodiment, the solubility of water in said organic hydrophilic solvent at 200° C. is at least 20 gram water per 100 gram of solvent, at least 30, at least 40, at least 50, at least 60, at least 70 or at least 80 gram water per 100 gram of solvent. According to an embodiment, said organic hydrophilic solvent is fully miscible with water at 200° C.

According to an embodiment, said organic hydrophilic solvent is selected from the group consisting of alkanols and ethers. According to an embodiment, said organic hydrophilic solvent comprises ethanol and/or isopropyl alcohol. According to an embodiment, said organic hydrophilic solvent comprises ethanol.

According to an embodiment, said first extract comprises at least one cannabinoids, at least two, at least three, at least four or at least five. According to an embodiment, the content of said cannabinoid in said extract is at least 0.3% by weight, at least 0.6%, at least 0.9%, at least 1.2%, at least 1.5%, at least 1.8%, at least 3.1%, at least 2.4%, at least 2.7%, or at least 3%.

According to an embodiment, the first extract comprises THC and/or THCa. According to an embodiment, the first extract comprises CBD and/or CBDa. According to an embodiment, the first extract comprises THC and/or THCa at a content of less than 1% by weight, less than 0.8%, less than 0.6%, less than 0.4% or less than 0.2%. According to an embodiment, the first extract comprises both CBD and/or CBDa and THC and/or THCa and the weight/weight ratio between CBD and/or CBDa and THC and/or THCa ((CBD+CBDa)/(THC+THCa)) is at least 10, at least 15, at least 20, at least 25 or at least 30.

According to an embodiment, said first extract further comprises at least one terpene, at least two, at least three, at least four or at least five. According to an embodiment, terpene content of said first extract is in the range between 0.05% and 1% by weight, between 0.1% and 0.9% or between 0.15% and 0.7%.

According to an embodiment, said first extract comprises water at concentration W1 by weight. According to an embodiment, W1 is at least 2% by weight, at least 4%, at least 6%, at least 8%, at least 10%, at least 12%. According to an embodiment, W1 is less than 22% by weight, less than 20%, less than 18%, less than 16%, less than 15%, less than 14%, less than 13% or less than 12%. According to an embodiment, said first extract comprises an organic hydrophilic solvent, said solvent forms an azeotrope with water and water concentration in said first extract is greater than that in the azeotrope at same temperature. According to an embodiment, said organic hydrophilic solvent comprises ethanol and water concentration in said first extract is between 5% and 20% by weight, between 6% and 16% or between 7 and 15%.

According to an embodiment, said organic hydrophilic solvent comprises ethanol, W1 is in a range between 5% and 20% by weight and W2 is in the range between 20% and 40% by weight.

According to an embodiment, said first extract comprises wax. According to an embodiment, said first extract is provided by extracting cannabis plant material and said wax is extracted from said cannabis plant material. According to an embodiment, wax content in said first extract is determined by the nature of said cannabis plant material.

According to an embodiment, said first extract comprises at least one impurity at impurity to cannabinoid weight/weight ratio R1. As used herein, the term impurity refers to a compound other than a pharmaceutically desired cannabinoid and/or other than a pharmaceutically desired terpene and/or other than a pharmaceutically desired flavonoid.

According to an embodiment, said impurity comprises a pharmaceutically undesired cannabinoid, a pharmaceutically undesired terpene or both. According to an embodiment, said impurity comprises at least one pesticide and/or at least one herbicide. According to an embodiment, said impurity comprises a cannabis plant material component other than cannabinoids, terpenes and/or a product of degradation of such cannabis plant material components. According to an embodiment, said impurity comprises a cannabis plant material component other than wax. According to an embodiment, said impurity, as such or after heating, contributes to dark color of the extract. According to an embodiment, said impurity, as such or after heating, contributes to undesired flavor and/or aroma of the extract. According to an embodiment, said impurity, as such or after heating, interferes with formulating said extract. According to an embodiment, said impurity has a boiling point higher than 1500° C. According to an embodiment, said impurity is lipophilic in nature. According to an embodiment, said impurity has a solubility in 95% ethanol at 200° C. of at least 1 gram impurity per 100 gram ethanol.

According to an embodiment, the impurity to cannabinoid weight/weight ratio is R1. According to an embodiment, R1 is greater than 0.0005, greater than 0.001, greater than 0.005 or greater than 0.01. According to an embodiment, R1 is less than 0.5, less than 0.1, less than 0.05, less than 0.01 or less than 0.005.

According to an embodiment, said first extract forms a single phase. According to an embodiment, said first extract forms a single layer and forms no visible solid matter when kept unmixed for 1 hour.

According to an embodiment, said method comprises adding water to said first extract to reach water concentration W2 by weight, whereby a solid matter and a second extract are formed. As used herein, the term solid refers to any phase in the medium that is not part of a homogeneous liquid, e.g. haze, precipitate, floating solids, suspended solids, filterable matter, etc. As used herein, the term precipitate also refers to solid and the term precipitation refers to any form of solid formation. As used herein, the term filterable matter refers to matter that can be filtered out on a filter with a pore size of 0.5 micron.

Any form of adding water is suitable, e.g. mixing said first extract with water. Water addition can be conducted at any temperature. According to an embodiment, water is added while the temperature of said first extract is under the atmospheric boiling point of said organic hydrophilic solvent. According to an embodiment, W2/W1 is greater than 1.1, greater than 1.2, greater than 1.3, greater than 1.4, greater than 1.5, greater than 1.6, greater than 1.7, greater than 1.8, greater than 1.9, or greater than 2. According to an embodiment, W2/W1 is less than 3, less than 2.9, less than 2.8, less than 2.7, less than 2.6, or less than 2.5. According to an embodiment, said organic hydrophilic solvent comprises ethanol and W2 is less than 40% by weigh, less than 38%, less than 36%, less than 34% or less than 32%.

According to an embodiment, said method further comprises maintaining said first extract at a temperature of less than zero degrees Celsius for a duration of at least 1 hour, at least 5 hours, at least 10 hours, at least 15 hours or at least 20 hours, before said water addition, concurrently with water addition or after said water addition.

According to an embodiment, said first extract comprises cannabinoids, terpenes and impurities dissolved in said organic hydrophilic compound. According to an embodiment, said solutes are at a concentration below saturation, optionally even at a temperature of sub-zero Celsius. Without wishing to be limited by any theory, water addition might decreases the solubility of at least some of these solutes, which might results in some precipitation.

According to an embodiment, said method comprises separating said solid matter from said second extract, whereby separated solid matter and separated second extract are formed. Any form of separation is suitable, e.g. decantation, filtration and centrifugation. According to an embodiment, said separated second extract comprises said organic hydrophilic solvent, said at least one cannabinoid, water, optionally at least one terpene and optionally said at least one impurity at impurity to cannabinoid weight/weight ratio R2. According to an embodiment, said solid matter comprises said at least one impurity and optionally said cannabinoid and wax. According to an embodiment, said method further comprises separating organic hydrophilic solvent from said second extract. According to an embodiment, said separating organic hydrophilic solvent comprises evaporating said solvent. According to an embodiment, water is evaporated along with said organic hydrophilic solvent. According to an embodiment, said separating said organic hydrophilic solvent leads to the formation of a concentrated solvent-free or solvent-depleted extract. According to an embodiment, said separating said organic hydrophilic solvent leads to the formation of an aqueous layer and another layer comprising said concentrated solvent-free or solvent-depleted extract. According to an embodiment, said method comprises separating said aqueous layer from said layer of concentrated extract.

The inventors have surprisingly found that, while said water addition might induce the precipitation of both cannabinoid and impurity, a larger fraction of the impurity is precipitated, generating a second extract that is more pure (has lower impurity to cannabinoid ratio) compared with that in the first extract. Thus, according to an embodiment, the weight per weight ratio between said impurity and said cannabinoid in said separated second extract is smaller than that in the first extract, e.g. R2/R1 is less than 0.9, less than 0.8, less than 0.7, less than 0.6, less than 0.5, less than 0.4, less than 0.3 or less than 0.2. According to an embodiment, said water addition further induces precipitation of both cannabinoid and wax, but a larger fraction of the wax is precipitated, so that the weight per weight ratio between wax and said cannabinoid in said separated second extract is smaller than that in the first extract.

According to an embodiment, said water addition induces precipitation of a fraction of said cannabinoid along with impurities, leading to some loss of cannabinoid from said second extract to said separated solid. The inventors have found that at the embodiments of the present invention, while said second extract may contain less cannabinoid than in said first extract, the ratio between impurity and cannabinoid in said second extract is greater than that ratio in said first extract. The inventors have also found that at the embodiments of the present invention, major purification can be reached (i.e. a large fraction of the impurity can be precipitated) without suffering a major loss of said cannabinoid to said separated solid. Hence, according to an embodiment, the amount of said cannabinoid in said first extract is C1, the amount of said cannabinoid in said second extract is C2, and C2/C1 is greater than 0.5, greater than 0.6, greater than 0.7, greater than 0.8, greater than 0.9, or greater than 0.95.

According to an embodiment, said method further comprises producing a purified cannabis extract from said second extract. According to an embodiment, said producing comprises separating therefrom at least a fraction of said organic hydrophilic solvent.

According to an embodiment, further provided is a purified cannabis extract produced according to said method, which purified extract is characterized by having a lighter color compared with that of an extract produced by said method, except for adding one half the amount of water. According to an embodiment, said purified extract is characterized by having a lighter color compared with that of said first extract.

According to an embodiment, further provided is a purified cannabis extract produced according to said method, which purified extract is characterized by having a less astringent flavor compared with that of an extract produced by said method, except for adding one half the amount of water. According to an embodiment, said purified extract is characterized by having a less astringent flavor compared with that of said first extract.

According to an embodiment, said separated solid matter comprises at least one cannabinoid and said method further comprises combining said separated solid matter with a cannabinoid-comprising composition. According to an embodiment, said separated solid matter is mixed with cannabis plant material. According to an embodiment, said separated solid matter is mixed with an extract of cannabis plant material.

According to an embodiment, said separated solid matter comprises at least one cannabinoid and said method further comprises contacting said separated solid matter with an organic solvent, also referred to herein as a dissolving solvent, whereby a third extract is formed. According to an embodiment, said method further comprises combing said third extract with a cannabinoid-comprising composition. According to an embodiment, said dissolving solvent comprises ethanol. According to an embodiment, said third extract is mixed with an extract of cannabis plant material. According to an embodiment, said third extract is mixed with cannabis plant material. According to an embodiment, said third extract is mixed with cannabis plant material to form a homogeneous mixture. According to an embodiment, said method further comprises separating said organic solvent form said homogeneous mixture.

According to an embodiment, further provided is a method for producing a purified cannabis extract comprising (i) providing a cannabis plant material comprising at least one cannabinoid and at least one impurity at impurity to cannabinoid weight/weight ratio R3; (ii) contacting said cannabis plant material for a duration of at least 0.1 minute, with an extractant comprising an organic hydrophilic solvent and W3 water, wherein the temperature of said extractant is T1, whereby a fourth extract and residual plant material are formed, which fourth extract comprises said organic hydrophilic solvent, at least one cannabinoid, water, optionally at least one terpene, optionally wax, and at least one impurity at impurity to cannabinoid weight/weight ratio R4; and (iii) separating said fourth extract from said residual plant material, wherein (a) said organic hydrophilic solvent is fully miscible with water at T1 and W3 is greater than 10% by weight, or the solubility of said organic hydrophilic solvent in water at T1 is at least 20 gram solvent per 100 gram water and W3 is at least one tenth of saturation water concentration at T1, (b) T1 is sub-zero Celsius; and (c) R4/R3 is less than 0.9.

According to an embodiment, impurity to cannabinoid weight/weight ratio R3 is in the range between 1:1 and 0.005:1. Any form of contacting is suitable, e.g. in a mixture, in a column, batch, continuous, counter-current, etc. According to an embodiment, contacting duration is greater than 0.1 minute, greater than 0.5 minute, greater than 1 minutes, greater than 2 minute, greater than 3 minutes, or greater than 5 minutes. According to an embodiment, contacting duration is less than 30 minutes, less than 25 minutes, less than 20 minutes, or less than 15 minutes. Any form of contacting said plant material with an extractant is suitable, e.g. in a mixture, in a column, batch, continuous, counter-current, etc. Any form of separating said fourth extract from said residual plant material is suitable, e.g. decanting, filtering, centrifuging, etc.

According to an embodiment, said extractant comprises an organic hydrophilic solvent. According to an embodiment, said organic hydrophilic solvent forms at least 60% of said extractant, at least 70% or at least 80%.

According to an embodiment, the boiling point of said organic hydrophilic solvent is less than 100 degrees Celsius. According to an embodiment, the solubility of said organic hydrophilic solvent in water at 20° C. is at least 20 gram solvent per 100 gram of water, at least 30, at least 40, at least 50, at least 60, at least 70 or at least 80 gram solvent per 100 gram of water. According to an embodiment, the solubility of water in said organic hydrophilic solvent at 20° C. is at least 20 gram water per 100 gram of solvent, at least 30, at least 40, at least 50, at least 60, at least 70 or at least 80 gram water per 100 gram of solvent. According to an embodiment, said organic hydrophilic solvent is fully miscible with water at 20° C.

According to an embodiment, said organic hydrophilic solvent is selected from the group consisting of alkanols and ethers. According to an embodiment, said organic hydrophilic solvent comprises ethanol and/or isopropyl alcohol. According to an embodiment, said organic hydrophilic solvent comprises ethanol.

According to an embodiment, said extractant comprises W3 water. According to an embodiment, said organic hydrophilic solvent forms an azeotrope with water and water concentration in said extractant is greater than that in the azeotrope at same temperature. According to an embodiment, said organic hydrophilic solvent is fully miscible with water at T1 and W3 is greater than 10% by weight, greater than 15%, greater than 20%, greater than 25% or greater than 25%. According to another embodiment, said organic hydrophilic solvent is only partially miscible with water at T1 and W3 is at least one tenth of saturation water concentration at T1, at least two, at least three or at least four tenths. For example, if water solubility in said organic hydrophilic solvent at 20° C. is 60 gram per 100 gram solvent, W3 is at least 6 gram per 100 gram solvent, at least 12 gram, at least 18 gram or at least 24 grams per 100 gram solvent.

According to an embodiment, T1 is sub-zero Celsius, less than minus 5° C., less than minus 10° C., less than 15° C. or less than 20° C.

According to an embodiment, impurity proportion in the purified cannabis extract is less than that in said provided cannabis plant material. According to an embodiment, R4/R3 is less than 0.9, less than 0.8, less than 0.7, less than 0.6, less than 0.5, less than 0.4, less than 0.3 or less than 0.2.

According to an embodiment, said method further comprises (i) adding water to said fourth extract to reach water concentration W4 by weight, whereby a solid matter and a fifth extract are formed; which fifth extract comprises said organic hydrophilic solvent, said at least one cannabinoid, water, optionally at least one terpene and optionally said at least one impurity at impurity to cannabinoid weight/weight ratio R5; (ii) separating said solid matter from said fifth extract, whereby separated solid matter and separated fifth extract are formed; and optionally separating organic hydrophilic solvent from said fifth extract; wherein (a) W4/W3 is greater than 1.1; and (b) R5/R4 is less than 0.9. According to an embodiment, W4/W3 is greater than 1.2, greater than 1.3, greater than 1.3, greater than 1.4, or greater than 1.5. According to an embodiment, R5/R4 is less than 0.8, less than 0.7, less than 0.6, less than 0.5, less than 0.4, less than 0.3 or less than 0.2.

According to an embodiment, said impurity comprises a pharmaceutically undesired cannabinoid, a pharmaceutically undesired terpene and/or a pharmaceutically undesired flavonoid. According to an embodiment, said impurity comprises at least one pesticide and/or at least one herbicide. According to an embodiment, said impurity comprises a cannabis plant material component other than cannabinoids and terpenes and/or a product of degradation of such cannabis plant material components. According to an embodiment, said impurity comprises a cannabis plant material component other than wax. According to an embodiment, said impurity, as such or after heating, contributes to dark color of the extract. According to an embodiment, said impurity, as such or after heating, contributes to undesired flavor and/or aroma of the extract. According to an embodiment, said impurity, as such or after heating, interferes with formulating said extract. According to an embodiment, said impurity has a boiling point higher than 150° C. According to an embodiment, said impurity is lipophilic in nature. According to an embodiment, said impurity has a solubility in 95% ethanol at 20° C. of at least 1 gram impurity per 100 gram ethanol.

According to an embodiment, said water addition induces precipitation of a fraction of said cannabinoid along with impurities, leading to some loss of cannabinoid from said fifth extract to said separated solid matter. The inventors have found that at the embodiments of the present invention, major purification can be reached (i.e. a large fraction of the impurity can be precipitated) without suffering a major loss of said cannabinoid. Hence, according to an embodiment, the amount of said cannabinoid in said fourth extract is C3, the amount of said cannabinoid in said fifth extract is C4, and C4/C3 is greater than 0.5, greater than 0.6, greater than 0.7, greater than 0.8, greater than 0.9, or greater than 0.95.

According to an embodiment, said method comprises maintaining said fourth extract at a temperature of less than zero degrees Celsius for a duration of at least one hour, at least 5 hours, at least 8 hours, at least 11 hours or at least 15 hours, before said water addition, concurrently with water addition or after said water addition.

According to an embodiment, said hydrophilic organic solvent comprises ethanol and W3 is in the range between 5% and 40% by weight, between 10% and 35% or between 15% and 30%.

According to an embodiment, said method further comprises producing a purified cannabis extract from said fifth extract. According to an embodiment, said producing comprises separating therefrom at least a fraction of said organic hydrophilic solvent.

According to an embodiment, further provided is a purified cannabis extract produced according to said method, which purified extract is characterized by having a lighter color compared with that of an extract produced by said method, except for using an extractant with one half W3 water, except for contacting with an extractant at a temperature of above zero Celsius or both. According to an embodiment, said purified extract is characterized by having a lighter color compared with that of said fourth extract.

According to an embodiment, further provided is a purified cannabis extract produced according to said method, which purified extract is characterized by having a less astringent flavor compared with that of an extract produced by said method, except for using an extractant with one half W3 water, except for contacting with an extractant at a temperature of above zero Celsius or both. According to an embodiment, said purified extract is characterized by having a less astringent flavor compared with that of said fourth extract.

EXAMPLES

Examples 1 and 2

First Extract Preparation

Cannabis buds were dried to about 13% moisture and ground to particles of about 1 millimeter. Samples of the ground material were introduced into vials and ethanol solutions at selected temperatures were added. The vials were shacked for a selected time followed by filtering out the residual ground material. See details in Table 1.

TABLE 1

| | | Ground material | Ethanol | | | Shacking |
|---|---|---|---|---|---|---|
| Example # | Strain name | Amount (gram) | Concen. (%) | Temp. (° C.) | Amount (gram) | Time (minutes) |
| 1 | PHD (Better, Israel) | 100 | >95 | (−)20 | 1000 | 10 |
| 2 | PHD (Better, Israel) | 100 | 70-5 | 25 | 1000 | 30 |
| Comparative 1 | PHD (Better, Israel) | 100 | >95 | 25 | 1000 | 30 |

Examples 3 and 4

Ethanol Evaporation and Decarboxylation

Filtrates formed in Examples 1 and 2 and in Comparative Examples 1 were concentrated up by evaporating the ethanol therefrom. The formed concentrates were heat treated in order to induce decarboxylation. Cannabinoids concentrations in the formed extracts were analyzed on HPLC. Details and results are summarized in Table 2.

TABLE 2

| | Filtrate of | Decarboxylation | | Analysis | | |
|---|---|---|---|---|---|---|
| Examples # | Examples # | Temp (° C.) | Duration (min) | THC (%) | CBD (%) | Extract observation |
| 3 | 1 | 120 | 90 | 3 | 68 | Light brown |
| 4 | 2 | 100 | 90 | 2.75 | 42.75 | Light brown |
| Comparative 2 | Comparative 1 | 120 | 45 | 3 | 64 | Dark brown |

These results show that extracts formed by extracting cannabis plant material at a short contact time and at a temperature of minus 20° C. and have a lighter color compared with ones extracted at 25° C. with an extractant containing less than 25% water. The same is true for extracts formed on extraction with an extractant containing about 30% water. Less color-inducing impurities are extracted in both cases.

Example 5

Water Addition and Precipitate Separation

Cannabis buds were dried to about 13% moisture and ground to particles of about 1 millimeter. Samples of the ground material were introduced into vials and >95% ethanol solutions at 25° C. were added. The vials were shacked for 30 minutes, followed by filtering out the residual ground material to form a first filtrate.

Water was added to 100 gram of the first filtrate in a vial, followed by gentle shaking of the vial. A dark precipitate was formed. The Vial was kept in a freezer overnight. Then, the precipitate was removed by filtration on a 0.45 micron filter. The formed second filtrate was further concentrated up by evaporation.

Another 100 gram fraction of the first filtrate was concentrated up by removing 75% of the ethanol therein and then introduced to a vial. No precipitate was observed. The vial was kept in a freezer overnight, after which some suspension was observed. The vial content was filtered on a 0.45 micron filter. The formed third filtrate was further concentrated up by evaporation.

The two formed concentrates were heat treated in order to induce decarboxylation. Cannabinoids concentrations in the formed extracts were analyzed on HPLC. Details and results are summarized in Tables 3 and 4.

TABLE 3

| Examples # | Water conc. before water addition (%) | Partial concen. | Fraction of ethanol evaporated (%) | Water addition | Water conc. during 0.45 micron filtration (%) |
|---|---|---|---|---|---|
| 5 | <5% | No | 0 | Yes | 30 |
| Comparative 3 | <5% | Yes | 75 | No | <5% |

TABLE 4

| | | | | | Cannbinoids content | | |
|---|---|---|---|---|---|---|---|
| | Decarboxylation | | Analysis | | Before water | After water | |
| Examples # | Temp (° C.) | Duration (min) | THC (%) | CBD (%) | addition (gram) | addition (gram) | Extracts observation |
| 5 | 100 | 120 | 3 | 88 | 7.92 | 5.54 | Light brown |
| Comparative 3 | 120 | 120 | 3 | 64 | 7.92 | | Dark brown |

Water addition resulted in precipitation of impurities contributing to the color of the extract. About 30% of the cannabinoids co-precipitated.

Example 6

Cannabinoid Loss to Precipitate

The precipitate filtered on the 0.45 micron filter in Example 5 was mixed with 100 gram of 95% ethanol and the formed solution was filtered on 0.45 micron filter. The formed filtrate was concentrated up by evaporating 75% of the ethanol. No precipitate was observed. The concentrated solution was analyzed on HPLC. It was found to contain 2.25 gram cannabinoids.

Example 7

Taste Evaluation

Extracts formed in Examples 3 and 5 and in Comparative Example 3, were diluted in canola oil to form oil diluted extracts samples with CBD concentration of 10%. Five people tasted those three samples. They all indicated that the tastes of the oil diluted extracts produced in Example 3 and 5 were much less astringent compared with oil diluted extract produced in Comparative Example 3.

The invention claimed is:

1. A method for producing a cannabis extract comprising:
   (i) extracting cannabis material of one or more of trimmed leaves of cannabis, trimmed flowers of cannabis, and buds of cannabis, with ethanol and/or isopropanol at a water concentration of 4%-15% by weight of the ethanol and/or isopropanol to yield a spent cannabis material and a first extract of the cannabis material comprising ethanol and/or isopropanol at a water concentration of 4%-15%, by weight, at least one cannabinoid, at least one terpene, wax, and at least one impurity other than the cannabinoid, the terpene, and the wax, at an impurity to cannabinoid weight ratio of R1;
   (ii) separating said first extract from said spent cannabis material to yield a separated first extract;
   (iii) adding water to said separated first extract to reach a water concentration of 20%-40% by weight, whereby a solid matter and a second extract are formed;
   (iv) separating said solid matter from said second extract, wherein the second extract comprises said ethanol and/or isopropanol, said at least one cannabinoid, water, at least one terpene, wax, and at least one impurity, at an impurity to cannabinoid weight ratio of R2; and
   (v) separating the ethanol and/or isopropanol from said second extract to yield the cannabis extract, wherein the solubility of said ethanol and/or isopropanol in water at 20° C. is at least 20 grams of solvent per 100 grams of water, and
   R2/R1 is less than 0.9.

2. The method of claim 1, wherein cannabinoid amount in said first extract is C1, wherein cannabinoid amount in said second extract is C2, and wherein C2/C1 is greater than 0.5.

3. The method of claim 1, further comprising maintaining said first extract at a temperature of less than zero degrees Celsius for a duration of at least 1 hour before said adding water, concurrently with said adding water or after said adding water.

4. The method of claim 1, further comprising combining said separated solid matter with a different cannabis plant material.

\* \* \* \* \*